United States Patent [19]

Galleguillos et al.

[11] Patent Number: 5,549,887
[45] Date of Patent: * Aug. 27, 1996

[54] ANTIPERSPIRANT DEODORANT COMPOSITIONS

[75] Inventors: Ramiro Galleguillos, Glendale Heights; Maximo M. Panitch, Skokie; Anjana K. Jadav, Chicago, all of Ill.

[73] Assignee: Helene Curtis, Inc., Chicago, Ill.

[*] Notice: The term of this patent shall not extend beyond the expiration date of Pat. No. 5,534,245.

[21] Appl. No.: 355,636

[22] Filed: Dec. 14, 1994

Related U.S. Application Data

[63] Continuation-in-part of Ser. No. 199,763, Feb. 22, 1994.

[51] Int. Cl.$^6$ .............................. A61K 7/34; A61K 7/38
[52] U.S. Cl. ................................. 424/66; 424/68
[58] Field of Search .................... 424/65, 66, 68

[56] References Cited

U.S. PATENT DOCUMENTS

| | | | |
|---|---|---|---|
| 2,607,658 | 8/1952 | Govett et al. | 23/14 |
| 2,645,616 | 7/1953 | Govett et al. | 252/317 |
| 2,876,163 | 3/1959 | Garizio et al. | 167/90 |
| 3,255,082 | 6/1966 | Barton | 167/90 |
| 3,740,421 | 6/1973 | Schmolka | 424/65 |
| 3,822,238 | 7/1974 | Blair et al. | 260/75 NK |
| 3,975,350 | 8/1976 | Hudgin et al. | 260/30.4 N |
| 4,120,948 | 10/1978 | Shelton | 424/66 |
| 4,156,066 | 5/1979 | Gould | 528/73 |
| 4,156,067 | 5/1979 | Gould | 528/73 |
| 4,225,550 | 3/1981 | Gould | 528/44 |
| 4,268,499 | 5/1981 | Keil | 424/68 |
| 4,278,655 | 7/1981 | Elmi | 424/47 |
| 4,350,605 | 9/1982 | Hughett | 252/305 |
| 4,359,558 | 11/1982 | Gould et al. | 525/454 |
| 4,451,635 | 5/1984 | Gould et al. | 528/71 |
| 4,454,309 | 6/1984 | Gould et al. | 525/454 |
| 4,673,570 | 6/1987 | Soldati | 424/66 |
| 4,725,430 | 2/1988 | Schamper et al. | 424/66 |
| 4,743,673 | 5/1988 | Johnston et al. | 528/60 |
| 4,822,602 | 4/1989 | Sabatelli | 424/65 |
| 4,904,466 | 2/1990 | Carson | 424/76.3 |
| 5,000,955 | 3/1991 | Gould et al. | 424/409 |

FOREIGN PATENT DOCUMENTS

| | | | |
|---|---|---|---|
| 0448278 | 9/1991 | European Pat. Off. | A61K 7/38 |
| 0450597 | 10/1991 | European Pat. Off. | A61K 47/10 |
| 0512770 | 11/1992 | European Pat. Off. | A61K 7/48 |
| 0550960 | 7/1993 | European Pat. Off. | A61K 7/32 |
| WO91/15191 | 10/1991 | WIPO | A61K 7/38 |
| WO92/05767 | 4/1992 | WIPO | A61K 7/34 |
| WO92/19222 | 11/1992 | WIPO | A61K 7/32 |

OTHER PUBLICATIONS

Remingtons Pharmaceutical Sciences Eighteen Edition 1990. p. 761.
Finch, C. A., ed., *Chemistry and Technology of Water Soluble Polymers*, pp. 105–107, Plenum Press, NY, NY (1983).
*Encyclopedia of Chemical Technology*, vol. 23, pp. 848–863, Wiley Interscience, NY, NY (1988).
Shibayama, M. et al., "Gelation of Poly(vinyl alcohol)–Vanadate Aqueous Solutions," *Macromolecules*, vol. 26, pp. 623–627 (1993).
Sinton, S. W., "Complexation Chemistry of Sodium Borate with Poly(vinyl alcohol) and small diols," *Macromolecules*, vol. 20, pp. 2430–2441 (1987).
C. Fox, "Antiperspirants & Deodorants Review and Update", *Cosmetics & Toiletries*, 100, pp. 27–41 (1985).
Anon., "Deodorant & Antiperspirant Formulary", *Cosmetics & Toiletries*, 100, pp. 65–75 (1985).
P. R. Howard et al. "Chapter 12–Systems Approach for Rheology Control", in *Polymers as Rheology Modifiers*, pp. 207–221.
R. L. Goldemberg, et al. "Silicones in Clear Formulations" *D&CI*, Feb. 1986, pp. 34–44.

*Primary Examiner*—C. Warren Ivy
*Assistant Examiner*—Evelyn Huang
*Attorney, Agent, or Firm*—Marshall, O'Toole, Gerstein, Murray & Borun

[57] ABSTRACT

Gelled or solid antiperspirant compositions comprising an antiperspirant compound, a borate crosslinker, a hydrophilic polymeric binder, a carrier, and, optionally, a softening agent, are disclosed.

29 Claims, No Drawings

ANTIPERSPIRANT DEODORANT COMPOSITIONS

CROSS-REFERENCE TO RELATED APPLICATION

This is a continuation-in-part application of pending U.S. Application Ser. No. 08/199,763, filed Feb. 22, 1994.

FIELD OF THE INVENTION

The present invention is directed to antiperspirant compositions comprising an antiperspirant compound, like an astringent salt; a borate crosslinker, like boric acid; a hydrophilic polymeric binder, like a hydrophilic polyurethane having a molecular weight of at least about 10,000; a carrier; and optionally, a softening agent, like a nonionic surfactant. The antiperspirant compositions are gelled or solid compositions that typically are transparent, phase stable and essentially nonwhitening and nonstaining to skin and clothing after topical application; effectively deliver the antiperspirant compound to the skin; and exhibit excellent sensory properties. The present invention also is directed to methods of using the antiperspirant compositions.

BACKGROUND OF THE INVENTION

Antiperspirant compositions are well-known in the cosmetic art. An ideal antiperspirant composition is stable for the life of the composition, effectively delivers the antiperspirant compound to the skin, does not leave a visually-observable white residue on the skin or clothing, and is esthetically pleasing to the consumer.

Antiperspirant compositions are available in a variety of forms, such as aerosol suspensions; pump sprays; roll-on powders; emulsions or suspensions; and solid gels, waxes or suspensions. Antiperspirant compositions traditionally have been prepared as either oil-in-water emulsions or water-in-oil emulsions. Therefore, antiperspirant compositions of any form typically have a milky or opaque appearance and are manufactured by complex methods. Antiperspirant compositions prepared as emulsions often feel wet or oily when applied to the skin, and often remain tacky after the carrier of the composition evaporates. In addition, many emulsion-type antiperspirant compositions leave a white, staining residue on contacted skin or clothing.

Gelled emulsion-type antiperspirant compositions are used by rubbing an area of the body, such as the underarm, to apply a layer of the composition to the skin, and thereby reduce odor and/or perspiration. Gelled or solid antiperspirant compositions preferably possess the esthetic properties of nonbrittleness, smoothness, nonoiliness and nontackiness. Clarity, or transparency, of antiperspirant compositions also is a long-sought desirable esthetic property. Another highly desirable, but hard to achieve, esthetic property is avoiding a visible residue, e.g., a white layer, that is left on the skin or clothing after the antiperspirant composition is applied.

Nonemulsified antiperspirant compositions also are known in the art. However, nonemulsified compositions often require shaking prior to each use in order to redisperse the insoluble antiperspirant compound that has separated from the composition. Nonemulsified antiperspirant compositions that do not require shaking prior to each use, such as an antiperspirant creme or paste, typically include a relatively high percentage of suspending agents, like an organoclay. The presence of an organoclay in an antiperspirant composition is a principal source of the whitening and staining of skin and clothing.

Investigators have searched for antiperspirant compositions, and especially transparent antiperspirant compositions, that display the above-listed desirable properties. A gelled or solid antiperspirant composition is difficult to formulate and manufacture because the composition requires sufficient firmness to withstand rubbing across the skin to deliver a sufficient amount of the antiperspirant compound to the skin, and the composition also should be nonbrittle to resist fracturing and crumbling. Additional formulation parameters include viscosity control, lack of syneresis and nontackiness. Transparent, gelled or solid antiperspirant compositions are more difficult to formulate because of the added requirement of transparency.

A transparent gelled or solid antiperspirant composition which has esthetic and functional properties equal to or better than presently-available antiperspirants compositions is highly desired by consumers. However, providing a commercially-acceptable, transparent gelled or solid antiperspirant composition requires overcoming several formulation and manufacturing problems.

Transparent antiperspirant compositions, especially in the gel or solid, i.e., stick, form, are particularly favored by consumers because such transparent products are esthetically-appealing and project the appearance of product purity, safety, good performance and being non-whitening. However, due to the instability and the difficult manufacture of transparent compositions, transparent antiperspirant compositions are not readily available to consumers.

Solid antiperspirant compositions are divided into three main classes, i.e., compressed powder sticks, gel sticks and wax sticks. Each of these classes has advantages, but each class also has particular disadvantages. Compressed powder sticks for example are frequently brittle and hard, and leave a cosmetically-unacceptable powdery residue after application. Frequently, wax-based products are cosmetically unacceptable because of such factors as hardness, greasiness and tackiness. The opacity of wax sticks and the visually-observable white residue remaining after application also are esthetically undesirable.

Gel-type solid antiperspirant compositions have several advantages over both compressed powder sticks and wax sticks. For example, the gelled antiperspirant compositions leave less residue or dust on the skin. The gelled antiperspirant compositions also glide easily over the skin surface resulting in an easy and comfortable application of the composition.

However, the preparation of antiperspirant compositions in the form of an effective and stable gel is difficult. For example, a critical ingredient in gelled antiperspirant compositions is the gelling agent. Many prior gelled antiperspirant compositions comprise gelled hydroalcoholic solutions including a gelling agent, such as sodium stearate, to form the gel. However, common gelling agents cannot be used in the presence of acidic antiperspirant compounds because of an interaction between the gelling agent, which is alkaline, and the antiperspirant compound.

Prior transparent, gelled or solid antiperspirant compositions also typically were divided into three main classes. One of these classes is the optically-clear gelled emulsion compositions. These compositions include a water phase and an oil phase. The oil phase is suspended in the water phase by using a sufficient amount of an appropriate emulsifier or emulsifiers. The emulsions conventionally contained waxes, silicones, clays and emollients. The optically-clear gelled emulsion compositions are illustrated in U.S. Pat. Nos. 4,673,570, 4,268,499, 4,278,655, and 4,350,605; EP 0 450 597; and in "Deodorant and Antiperspirant Formulary", *Cosmetics & Toiletries*, Dec. 12, 1985, vol. 100, p. 65–75.

The optically-clear gelled emulsion compositions often exhibit the disadvantages of composition instability during storage; the development of a hazy or milky appearance during storage; a stringy, tacky, oily consistency and other undesirable esthetics. In addition, the emulsion gel compositions often leave a visible residue, in the form of a white layer, on the skin or clothing. Another disadvantage of optically-clear gelled emulsion compositions is the complex method of preparing an optically-clear gelled emulsion composition. The method traditionally requires high shear rates during mixing, high processing temperatures, and a series of cooling and heating process steps. In one embodiment of the present invention, optically-clear gelled emulsion compositions are prepared by a simple method to provide antiperspirant compositions that overcome the above-described disadvantages of optically-clear gelled emulsion compositions.

A second class of transparent gelled or solid antiperspirant compositions is antiperspirant compositions thickened with 1,3:2,4-dibenzylidene-sorbitol (DBS) or DBS derivatives. Such transparent antiperspirant compositions are disclosed in U.S. Pat. Nos. 4,822,602 and 4,725,430; European Patent Publication 0 512 770; WO 91/15191; and WO 92/19222.

Transparent, gelled antiperspirant compositions thickened with DBS or DBS-type compounds have a major disadvantage in that the compositions are unstable in the presence of highly-acidic antiperspirant compounds at elevated temperatures. In addition, another disadvantage is the high temperature required for manufacturing DBS-thickened compositions (i.e., about 230° F. to about 240° F.).

The third class of transparent gelled or solid antiperspirant compositions is the acid-base complex gels. These transparent antiperspirant compositions are prepared by interacting the active antiperspirant compound with a carboxylic acid salt. Transparent acid-based complex gels are disclosed, for example, in U.S. Pat. Nos. 3,255,082 and 2,876,163; and in European Publication No. 0 448 278.

For example, EP 0 448 278 discloses complexing an antiperspirant aluminum salt with ammonium acetate. U.S. Pat. No. 2,876,163 discloses complexing an antiperspirant aluminum salt with various water-soluble inorganic salts, like an alkali metal oxide, hydroxide, or carbonate, or a salt of an organic or inorganic acid, such as sodium carbonate, sodium phosphate, or sodium glutamate.

This third class of transparent antiperspirant compositions has a major disadvantage in that the active antiperspirant compound is partially deactivated by the salt, thereby reducing the efficacy of the antiperspirant compound and, accordingly, the antiperspirant composition. In addition, the resulting gels or solids are very brittle, tacky, and/or possess other undesirable esthetic properties, such as in the compositions disclosed in U.S. Pat. No. 3,255,082, which are emulsions or sols and therefore are often opaque.

Govett et al. U.S. Pat. Nos. 2,607,658 and 2,645,616 disclose similar gels comprising an aluminum chlorhydroxy complex and a borate.

Although numerous patents disclose transparent gelled or solid antiperspirant compositions, the gelled compositions designated as clear or transparent do not have the clarity desired by consumers. Some transparent antiperspirant compositions also exhibit synersis, or phase separation, during storage. Moreover, many of the prior art transparent compositions become cloudy or hazy after standing for a period of time. Typically, haziness increases to such an extent that the composition is cloudy and has little or no transparency about a month after preparation. Antiperspirant compositions conventionally have a product life in excess of one month. Therefore, the length of time the composition retains its transparency is an important esthetic property.

Investigators have continually sought to provide a gelled or solid antiperspirant composition having both long-term stability and sufficient esthetic and functional properties for consumer acceptance. These esthetic and functional properties include transparency, a sufficient hardness for application to the skin, a low degree of brittleness to resist fracture and crumbling of the composition, no visually-observable whitening of the skin and clothing, and the ability to effectively deliver the antiperspirant compound to the skin without providing a tacky or sticky feeling. The present invention is directed to providing gelled or solid antiperspirant compositions, and preferably transparent compositions, exhibiting these consumer-acceptable esthetic and functional properties.

SUMMARY OF THE INVENTION

The present invention relates to gelled or solid antiperspirant compositions having improved efficacy and esthetics, and to methods of using the antiperspirant compositions. More particularly, the present invention is directed to a transparent, gelled or solid antiperspirant composition comprising an antiperspirant compound; a borate crosslinker; a hydrophilic polymeric binder; a carrier; and, optionally, a softening agent.

In particular, the gelled or solid antiperspirant compositions comprise:

(a) about 1% to about 40% by weight of an antiperspirant compound, like an astringent salt;

(b) about 0.5% to about 10% by weight of a borate crosslinker, like boric acid, sodium tetraborate, or a mixture thereof;

(c) about 0.005% to about 10% by weight of a hydrophilic polymeric binder, like a hydrophilic polyurethane having a weight average molecular weight of at least about 10,000;

(d) a carrier; and (e) optionally, 0% to about 15% by weight of a softening agent, like a nonionic surfactant. The transparent antiperspirant compositions are acidic in nature, having a pH of about 2 to about 6.

The transparent, gelled or solid antiperspirant compositions maintain composition clarity over extended storage periods, are essentially nonstaining and nonwhitening to skin and clothing, effectively deliver the antiperspirant compound to the skin, are nonbrittle, and exhibit excellent esthetic and functional properties, including sensory properties, for consumer acceptance. The present antiperspirant compositions remain transparent for at least six months when stored at room temperature.

In a preferred embodiment, the transparent gelled antiperspirant composition comprises:

(a) about 5% to about 30% by weight of an aluminum or zirconium astringent salt, or combination thereof;

(b) about 0.8% to about 7% by weight of a borate crosslinker;

(c) about 0.01% to about 5% by weight of a hydrophilic polymeric binder selected from the group consisting of an ethoxylated, propoxylated or carboxylated hydrophilic polyurethane having a weight average molecular weight of at least about 20,000, a polyethylene glycol having a weight average molecular weight of at least 100,000, a water-soluble cellulosic polymer, and mixtures thereof;

(d) a carrier; and (e) optionally, 0% to about 12% by weight of a nonionic surfactant, wherein the transparent antiperspirant composition has a pH of about 3 to about 5.

In another preferred embodiment, the transparent, gelled or solid antiperspirant compositions include a hydrophobic compound to improve a particular esthetic or functional property of the antiperspirant compound. The hydrophobic compound can be a siloxane or a hydrocarbon, for example, and is included in the transparent antiperspirant composition in an emulsified form.

The present invention also relates to methods of treating or preventing malodors associated with human perspiration, especially underarm odor. The methods comprise topically applying an effective amount of a gelled or solid antiperspirant composition of the present invention to the skin of a human.

The above and other advantages and novel features of the present invention will become apparent from the following detailed description of the preferred embodiments of the invention.

DETAILED DESCRIPTION OF THE PREFERRED EMBODIMENTS

A gelled or solid antiperspirant composition of the present invention comprises an antiperspirant compound, a borate crosslinker, a hydrophilic polymeric binder, a carrier, and, optionally, a softening agent. In particular, the gelled or solid antiperspirant compositions have a pH of about 2 to about 6 and comprise:

(a) about 1% to about 40% by weight of an antiperspirant compound;

(b) about 0.5% to about 10% by weight of a borate crosslinker;

(c) about 0.005% to about 10% by weight of a hydrophilic polymeric binder;

(d) a carrier; and (e) optionally, 0% to about 15% by weight of a softening agent, such as a surfactant. Typically, the antiperspirant compositions are transparent. As used here and hereinafter, the term "transparent" is defined as at least 50% transmittance determined spectrophotometrically at 700 nm (nanometers).

The transparent gelled antiperspirant compositions are stable to phase separation, do not become hazy or milky during storage, and exhibit exceptional esthetic and functional properties. The antiperspirant compositions are nonbrittle, nonstringy and nontacky, and are capable of effectively delivering the antiperspirant compound to the skin, without leaving a visually-observable white residue on the skin or clothing, i.e., are essentially nonwhitening.

The present gelled antiperspirant compositions incorporate any of the antiperspirant compounds known in the art, such as the astringent salts. The astringent salts include organic and inorganic salts of aluminum, zirconium, zinc, and mixtures thereof. These astringent salts are polymeric in nature, and preferably contain hydroxyl moieties for interaction with a borate. The anion of the astringent salt can be, for example, sulfate, chloride, chlorohydroxide, alum, formate, lactate, benzyl sulfonate or phenyl sulfonate. Exemplary classes of antiperspirant astringent salts include aluminum halides, aluminum hydroxyhalides, zirconyl oxyhalides, zirconyl hydroxyhalides, and mixtures thereof.

Exemplary aluminum salts include aluminum chloride and the aluminum hydroxyhalides having the general formula $Al_2(OH)_xQ_y \cdot XH_2O$, wherein Q is chlorine, bromine or iodine; x is about 2 to about 5; x+y is about 6, wherein x and y are not necessarily integers; and X is about 1 to about 6. Exemplary zirconium compounds include zirconium oxy salts and zirconium hydroxy salts, also referred to as zirconyl salts and zirconyl hydroxy salts, and represented by the general empirical formula $ZrO(OH)_{2-nz}L_z$, wherein z varies from about 0.9 to about 2 and is not necessarily an integer; n is the valence of L; 2-nz is greater than or equal to 0; and L is selected from the group consisting of halides, nitrate, sulfamate, sulfate, and mixtures thereof.

The antiperspirant compound is present in the gelled antiperspirant composition in an amount of about 1% to about 40%, and preferably about 5% to about 30%, by weight of the composition. To achieve the full advantage of the present invention, the antiperspirant compound is present in an amount of about 10% to about 25% by weight of the antiperspirant composition.

The antiperspirant compounds are water-soluble. Exemplary antiperspirant compounds therefore include, but are not limited to, aluminum bromohydrate, potassium alum, sodium aluminum chlorohydroxy lactate, aluminum sulfate, aluminum chlorohydrate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof. Numerous other useful antiperspirant compounds are listed in WO 91/19222 and in the *Cosmetic and Toiletry Fragrance Handbook*, The Cosmetic, Toiletry and Fragrance Association, Inc., Washington, D.C., p. 56, 1989, hereinafter the CTFA Handbook, incorporated herein by reference.

Preferred antiperspirant compounds are the aluminum-zirconium chlorides complexed with an amino acid, like glycine, and the aluminum chlorohydrates. Preferred aluminum-zirconium chloride glycine complexes have an aluminum (Al) to zirconium (Zr) ratio of about 1.67 to about 12.5, and a total metal (Al+Zr) to chlorine ratio (metal to chlorine) of about 0.73 to about 1.93. These antiperspirant compounds typically are acidic in nature, thereby providing a gelled antiperspirant composition having a pH less than 7, and typically having a pH of about 2 to about 6, and preferably about 3 to about 5.

In addition to the antiperspirant compound, a antiperspirant composition of the present invention also includes a borate crosslinker, like boric acid or sodium tetraborate. Exemplary borate crosslinkers include, but are not limited tog boric acid, sodium borate, borax (sodium tetraborate), sodium metaborate, boron oxide ($B_2O_3$), oligomers of boric acid, potassium pentaborate, potassium metaborate, sodium triborate, metaboric acid ($HBO_2$), ammonium hydrogen tetraborate, magnesium borate, barium metaborate, calcium metaborate, orthoboric acid, lithium metaborate, lithium tetraborate, zirconium metaborate, and mixtures thereof. The borate acts as a crosslinking agent to provide transparent antiperspirant compositions having sufficient structural integrity to perform as a gelled or stick deodorant. To achieve the full advantage of the present inventions the borate crosslinker is boric acid or sodium tetraborate.

The borate crosslinker is present in a gelled or solid antiperspirant composition in an amount of about 0.5% to about 10%, and preferably, about 1% to about 7%, by weight of the composition. To achieve the full advantage of the present invention, the gelled or solid antiperspirant composition includes about 3% to about 6%, by weight of the composition, of a borate crosslinker. As will be demonstrated in more detail hereinafter, as the amount of borate crosslinker in the antiperspirant composition is increased relative to a particular amount of antiperspirant compound, the antiperspirant composition increases in firmness and brittleness. Therefore, a person skilled in the art can select composition that retains its shape in the free form (i.e., is unsupported) at room temperature (i.e., about 25° C.) for at least one day. In the absence of a borate crosslinker, the antiperspirant composition has a gel-like consistency, but is flowable and therefore, commercially unsuitable as an antiperspirant stick product.

Other polybasic inorganic acids and salts were tested for an ability to crosslink with the antiperspirant compound. The following Examples 1 through 9 illustrate that various polybasic inorganic acids and salts are not capable of crosslinking the antiperspirant compound, whereas Examples 14 and 21 illustrate that a borate crosslinking agent can crosslink the antiperspirant compound. In each composition of Examples 1–9, no gel or solid formation was observed after standing for a period of two hours to two days. In Examples 2, 3, 4, 8 and 9, a white precipitate formed when the polybasic inorganic acid or salt was added to the composition.

| Ingredients | Example 1[1] | Example 2 | Example 3 | Example 4 | Example 5 | Example 6 | Example 7 | Example 8 | Example 9 |
|---|---|---|---|---|---|---|---|---|---|
| Antiperspirant compound | 25[1] | 25 | 22 | 22 | 22 | 22 | 22 | 22 | 22 |
| Propylene Glycol | 45 | 45 | 40 | 40 | 40 | — | — | 40 | — |
| Water | 25 | 25 | 33.4 | 35.7 | 33.4 | 73.4 | 68 | 33.4 | 73.4 |
| Polybasic Inorganic Acid | 5[3] | 5[4] | 4.6[5] | 2.3[5] | 4.6[6] | 4.6[6] | 10.0[6] | 4.6[7] | 4.6[7] |
| pH | 3.7 | 4.35 | 5.7 | 5.7 | 3.1 | 3.5 | 3.2 | 3.3 | 3.1 |
| Appearance | Clear, fluid solution | White precipitate, dark green solution | White precipitate, solution | White precipitate solution | Clear, fluid solution | Clear, fluid solution | Clear, fluid solution | White precipitate, solution | White precipitate, solution |

[1] the amount of each ingredient is expressed as % by weight of the total composition, all percents set forth the amount of each ingredient actually present in the composition;
[2] aluminum chlorohydrate (ACH), available commercially as CHLOROHYDROL, from Reheis, Inc., Berkeley Heights, New Jersey, added as a 50% weight percent solution of ACH in water;
[3] sodium metatungstenate;
[4] sodium metavanadate;
[5] trisodium phosphate;
[6] phosphoric acid; and
[7] silicic acid.

an amount of borate crosslinker relative to a particular amount of antiperspirant compound to provide a gelled antiperspirant composition through a solid antiperspirant composition. The antiperspirant composition preferably is transparent.

It is theorized, but not relied upon herein, that the borate crosslinker interacts with and crosslinks the antiperspirant compound, e.g., an aluminum chlorohydrate. Accordingly, the antiperspirant compound, which is oligomeric or polymeric in nature, is crosslinked by the borate crosslinker to thicken and gel the antiperspirant composition to form a transparent, gelled or solid antiperspirant composition. In particular, it is theorized, but not relied upon herein, that the crosslinking occurs through interaction of the hydroxyl groups of the antiperspirant compound with the borate ion to produce bridges. Consequently, the borate bridges introduce a sufficient number of crosslinking sites that provide either gelled transparent semisolid compositions or transparent solid antiperspirant compositions. Because the antiperspirant compound is acidic, the crosslinking reaction occurs under acidic conditions (i.e., pH of about 2 to about 6).

The borate crosslinking agent is essential to providing a gelled or solid antiperspirant composition. As used here and hereinafter, the term "gel" is defined as a nonflowable In contrast, a composition including only sufficient amounts of an antiperspirant compound, a borate crosslinker and an aqueous carrier is a transparent gel or solid. When too low an amount of borate crosslinking agent is used, transparent gels are not sufficiently firm to serve as a solid antiperspirant compound. However, when too high an amount of borate crosslinking agent is used, the solid compositions are too brittle for commercial use. Such brittle antiperspirant compositions easily fracture or crumble during use making such transparent solid antiperspirants commercially unacceptable.

Therefore, in addition to the antiperspirant compound and the borate crosslinker, a gelled or solid antiperspirant composition of the present invention also includes about 0.005% to about 10%, and preferably about 0.01% to about 5%, by weight of the composition, of a hydrophilic polymeric binder. To achieve the full advantage of the present invention, the hydrophilic polymeric binder is present in an amount of about 0.1% to about 3%, by weight of the composition.

The hydrophilic polymeric binder has a molecular weight of at least about 5,000. The hydrophilic polymeric binder also tolerates a pH of about 2 to about 6, and resists precipitation from solution in the presence of a relatively high salt concentration. Therefore, the hydrophilic polymeric binder is either a hydrophilic ionic polymer having a low charge density (e.g., an anionic polymer having a limited number of carboxyl groups) or, preferably, a nonionic polymer. The hydrophilic polymeric binder acts as a viscosity modifier or thickener, reduces the brittleness of solid antiperspirant compositions and does not contribute to whitening of skin or clothing.

As previously described, a gelled or solid antiperspirant composition including an antiperspirant compound, like an aluminum chlorohydrate, and a borate crosslinker, like boric acid, is a transparent, but often a very hard and brittle, composition that is not commercially acceptable. However, surprisingly, by including a sufficient amount of a hydrophilic polymeric binder, the antiperspirant composition remains transparent and firm, but the brittleness of the composition is reduced significantly. Accordingly, a transparent, gelled or solid antiperspirant composition of the present invention retains its structural integrity, is resistant to fracture and crumbling, and therefore is commercially acceptable.

A polymeric binder included in a transparent antiperspirant composition of the present invention is hydrophilic, and therefore is soluble or dispersible in polar liquids, like water, alcohols, glycols and polyols. As will be described in more detail hereinafter, such polar liquids are carriers of the antiperspirant compositions of the present invention. The hydrophilic polymeric binder also is soluble in, and does not precipitate from, a polar liquid in the presence of a relatively high salt concentration and at a pH of about 2 to about 6.

Exemplary hydrophilic polymeric binders include, but are not limited to, polyethylene glycols, polypropylene glycols, polyacrylamides, polymethacrylamides, polyvinyl alcohols, polyvinyl pyrrolidones, water-soluble cellulosic polymers, dimethicone copolyols, alkyl dimethicone copolyols, hydroxypropylmethylcellulose, hydroxyethyl cellulose, hydroxybutylmethylcellulose, carboxymethylcellulose, polyoxyethylene-polyoxypropylene copolymers, polyurethanes, and mixtures thereof, as long as the hydrophilic polymeric binder is water soluble or water dispersible, and has a weight average molecular weight of at least about 5,000. The weight average molecular weight of the hydrophilic polymeric binder can range from about 5,000 to about 5,000,000.

An especially useful class of hydrophilic polymeric binders is the hydrophilic polyurethanes having a weight average molecular weight of at least about 10,000, and preferably about 20,000 to about 300,000. A weight average molecular weight in excess of 300,000 is not detrimental, but hydrophilic polyurethanes of molecular weight greater than 300,000 are difficult to handle and disperse in the carrier of the antiperspirant composition.

The hydrophilic polyurethanes typically are ethoxylated and/or propoxylated at least at one terminal end, and are terminated with a hydroxyl group. Another class of useful hydrophilic polyurethanes is the carboxylated polyurethanes having a low charge density.

The hydrophilic polyurethanes can be prepared from an aliphatic diisocyanate, an aromatic diisocyanate, or a mixture thereof. An aliphatic diisocyanate is preferred. The diisocyanate is typically interacted with a low molecular weight glycol or triol, such as ethylene glycol, diethylene glycol, propylene glycol, glycerol, hexylene glycol, dipropylene glycol, or mixtures thereof, wherein the glycol or triol has at least two hydroxyl groups and a molecular weight up to about 200 to provide a polyurethane. The diisocyanate also can be reacted with a polymeric dihydroxy-terminated oligomer having a molecular weight of about 200 to 10,000 to provide a hydrophilic polyurethane. Exemplary oligomers include, but are not limited to polypropylene glycols, polyethylene glycols, polybutylene glycols, and mixtures thereof. Preferably, a diisocyanate is interacted both with a low molecular weight diol or triol and with an oligomer to provide a hydrophilic polyurethane.

Exemplary, but non-limiting, diisocyanates include trimethylhexamethylene diisocyanate, isophorone diisocyanate, decamethylene-1,10-diisocyanate, cyclohexane-1,2-diisocyanate, methylene bis(cyclohexyl-4-isocyanate), toluene-1,4-diisocyanate, toluene-2,6-diisocyanate, diphenylmethane-4,4'-diisocyanate, 3,3'-dimethyldiphenylmethane-4,4'-diisocyanate, m-phenylene diisocyanate, p-phenylene diisocyanate, chlorophenylene diisocyanate, hexamethylene-1,6-diisocyanate, tetramethylene-1,4-diisocyanate, cyclohexane-1,4-diisocyanate, naphthalene-1,5-diisocyanate, 1-methoxyphenyl-2,4-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dichlorophenyl-4,4'-diisocyanate, 2,2',5,5'-tetrachlorodiphenyl-4,4'-diisocyanate, trimethylhexamethylene diisocyanate, m-xylene diisocyanate, and mixtures thereof. The polyurethane backbone also can be substituted with hydroxyl or carboxyl groups to improve the water solubility or dispersibility of the hydrophilic polymeric binder. Preferred hydrophilic polyurethanes are disclosed in Gould et al. U.S. Pat. No. 5,000,955, incorporated herein by reference. Other useful hydrophilic polyurethanes are disclosed in U.S. Pat. Nos. 3,822,238; 4,156,066; 4,156,067; 4,255,550; and 4,743,673, also incorporated herein by reference.

Other useful classes of hydrophilic polymeric binders are the dimethicone copolyols and the alkyl dimethicone copolyols. These hydrophilic polymers have advantages such as being liquid at room temperature, being water soluble or dispersible, and being easily incorporated into the antiperspirant compositions of the present invention. In addition, because of their amphiphilic nature, these polymers provide good skin feel properties.

In particular, the alkyl dimethicone copolyols have the structural formula

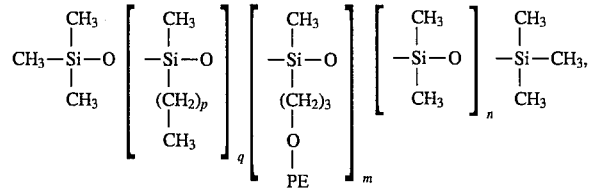

wherein p is a numeral from 0 through 24;

q is a numeral from 1 through 100;

m is a numeral from 1 through 40;

n is a numeral from 0 through 200; and

PE is $(C_2H_4O)_a(C_3H_6O)_b$-H having a molecular weight of about 250 to about 2000, wherein a and b are selected such that the weight ratio of $C_2H_4O/C_3H_6O$ is from 100/0 to 20/80. The alkyl dimethicone copolyols have a viscosity of about 1 to about 1,000 centipoise (cps).

An exemplary, but nonlimiting, alkyl dimethicone copolyol is cetyl dimethicone copolyol, available commercially as ABIL® EM 90 from Goldschmidt Chemical Corporation, Hopewell, Va.

A dimethicone copolyol also can be used as the hydrophilic polymeric binder. A dimethicone polyol is a dimethylsiloxane polymer having polyoxyethylene and/or polyoxypropylene side chains, such as DOW CORNING 3225C FORMULATION AID, available from Dow Corning Co., Midland, Mich., AMERSIL DMC-357, available from Amerchol Corp., Edison, N.J. or ABIL® B8852, available from Goldschmidt Chemical Corporation, Hopewell, Va.

Dimethicone copolyols have the structural formula

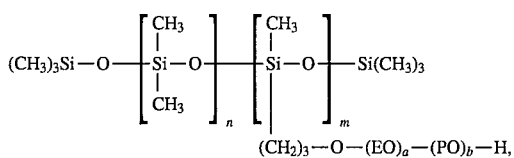

wherein EO is ethylene oxide ($C_2H_4O$), PO is propylene oxide ($C_3H_8O$), a and b are selected such that the weight ratio of EO/PO is 100/0 to 20/80, n is a numeral from 0 through 200, and m is a numeral from 1 through 40. The dimethicone copolyols have a viscosity of about 1 to about 600 centipoise.

The carrier of the present gelled or solid antiperspirant composition comprises water, water-soluble solvents and mixtures thereof. Exemplary carriers include, but are not limited to, water, ethylene glycol, propylene glycol, butylene glycol, propylene carbonate, dimethyl isosorbide, hexylene glycol, ethanol, n-butyl alcohol, n-propyl alcohol, isopropyl alcohol, and mixtures thereof. The carrier is present in a sufficient amount to solubilize, disperse or hydrate the essential and optional ingredients of the transparent antiperspirant composition.

As will be discussed in detail hereinafter, the transparent antiperspirant composition also can include a water-insoluble, or hydrophobic, compound, such as isohexadecene or 1-decene dimer, as long as a sufficient amount of an emulsifier also is included to emulsify the water-insoluble compound. Such water-insoluble compounds are not present as a carrier of the composition, but are included as optional ingredients for a specific purpose, such as faster drying time, better skin feel, or ease of application.

The present gelled or solid antiperspirant composition also can include an optional softening agent. The softening agent ensures efficacious delivery of the antiperspirant composition to the skin. The softening agent is present in the antiperspirant composition in an amount of 0% to about 15%, and preferably 0% to about 12%, by weight of the composition. The softening agent is a water-soluble compound, and typically is classified as an emollient or a surfactant.

Therefore, exemplary softening agents include, but are not limited to, polyoxyethylene ethers of fatty ($C_6$–$C_{22}$) alcohols, polyoxypropylene ethers of fatty ($C_6$–$C_{22}$) alcohols, dimethicone copolyols, polypropylene glycols, polyethylene glycols, ethoxylated alkylphenols, polyethylene glycol ethers of methyl glucose and mixtures thereof. The softening agents have an HLB (hydrophilic-lipophilic balance) value of at least about 6, and preferably at least about 8, and a weight average molecular weight of less than about 10,000, and preferably less than about 5,000. The HLB system of classifying surfactants is well-known to persons skilled in the art.

Specific, softening agents include methyl gluceth-20, methyl gluceth-10, $C_{12-15}$ alkyl benzoates, PEG-20 methyl glucose distearate, PEG-20 methyl glucose sesquistearate, PEG-200 castor oil, PEG-6, PEG-8, $C_{11-15}$ pareth-20, nonoxynol-9, octoxynol-10, nonyl nonoxynol-10, ceteth-8, ceteth-12, dodoxynol-12, laureth-15, PEG-20, PEG-3 castor oil, PEG-8 castor oil, PEG-20 castor oil, poloxamer 101, polysorbate 20, PPG-11 stearyl ether, dimethicone copolyol, steareth-20, and mixtures thereof. Other useful water-soluble softening agents are listed in the CTFA Handbook at pages 87 through 94, incorporated herein by reference.

In addition to the essential ingredients and the optional softening agent, the present gelled or solid antiperspirant compositions also can include other optional ingredients traditionally included in antiperspirant compositions. These optional ingredients include, but are not limited to, dyes, fragrances, preservatives, antioxidants, detackifying agents, deodorizing agents, and similar types of compounds. These optional ingredients typically are included in the antiperspirant composition in an amount of about 0.01% to about 10% by weight of the composition.

The present gelled or solid antiperspirant compositions typically are transparent. However, opacifying agents, pearlescent agents or fillers (e.g., titanium dioxide or a styrene-acrylamide copolymer) that render the antiperspirant composition nontransparent also can be included in the composition. The presence of such ingredients does not adversely effect the efficacy of the composition and are added to achieve a desired esthetic effect. Preferably, however, the antiperspirant composition is transparent, and typically is transparent unless rendered opaque by an intentionally-added optional ingredient.

In addition, a hydrophobic compound optionally can be included in the transparent antiperspirant compositions, as long as the hydrophobic compound is sufficiently emulsified in the antiperspirant composition. The hydrophobic compound can be, for example, an aliphatic hydrocarbon, a fatty ($C_8$–$C_{12}$) alcohol or a siloxane. These hydrophobic compounds improve the feel of the antiperspirant composition on the skin, allow easier application of the antiperspirant composition to the skin, and allow the skin to dry faster after application of the antiperspirant composition. The hydrophobic compounds are emulsified by compounds and methods well-known to those skilled in the art. Preferably, the hydrophobic compound is emulsified in a manner known to those skilled in the art to provide a transparent antiperspirant compound.

Hydrophobic aliphatic hydrocarbons incorporated into the transparent antiperspirant composition include, for example, isohexadecane, 1-decene dimer, mineral oils, nonvolatile hydrocarbon fluids, and hydrocarbons depicted in general structural formula (I), wherein n ranges from 2 to 5,

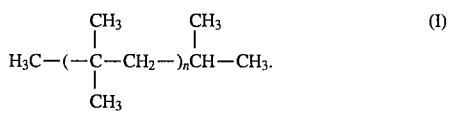

Volatile hydrocarbons, such as a hydrocarbon including about 10 to about 30 carbon atoms, have sufficient volatility to slowly volatilize from the skin after application of the antiperspirant composition. The volatile hydrocarbons provide benefits such as lubrication, a rich feel during application and faster drying. Specific volatile hydrocarbons having the structural formula (I) are the commercially-available compounds PERMETHYL 99A and PERMETHYL 101A, corresponding to compounds of general structure (I) wherein n is 2 and 3, respectively, available from Permethyl Corporation, Pottstown, Pa.

Siloxanes included in the transparent antiperspirant compositions provide the same benefits as the aliphatic hydrocarbons. Exemplary siloxanes include phenyltrimethicone; cyclic or linear, low molecular weight, volatile polydimethylsiloxanes known as cyclomethicones and dimethicones, respectively; and methicones. The cyclomethicones are low viscosity, low molecular weight, water-insoluble cyclic compounds having an average of about 3 to about 6-[O-Si($CH_3$)$_2$]-repeating group units per molecule. Cyclomethicones are available commercially under the tradenames SILICONE 344 FLUID and SILICONE 345 FLUID from Dow Corning Corporation, Midland, Mich., and SILICONE SF-1173 and SILICONE SF-1202 from General Electric, Waterford, N.Y., for example.

An example of a linear, low molecular weight, volatile dimethicone is the compound hexamethyldisiloxane, available commercially under the tradename DOW CORNING 200 FLUID, from Dow Corning Corp., Midland, Mich.

DOW CORNING 200 FLUID has a viscosity of 0.65 cs (centistokes), is highly volatile, is non-greasy, provides lubrication for topical application of the composition of the present invention to the skin. Other linear polydimethylsiloxanes, such as tetrabutoxypropyltrisiloxane, decamethyltetrasiloxane, octamethyltrisiloxane, and dodecamethylpentasiloxane, also have sufficient volatility to provide a dry feel after application. Another useful linear siloxane is bisphenylhexamethicone. Nonvolatile siloxanes also can be used as the hydrophobic compound. The volatile siloxanes and aliphatic hydrocarbons can be used alone, in combination, or in combination with nonvolatile siloxanes and/or nonvolatile aliphatic hydrocarbons.

Other suitable hydrophobic compounds include waxes, oils and fats, and water-insoluble emollients, like fatty ($C_8$–$C_{22}$) alcohols. The hydrophobic compounds are emulsified by including an emulsifying surfactant in the composition. Typically, the emulsifying surfactant is a nonionic surfactant. The particular amount and identity of the emulsifying surfactant can be determined by a person skilled in the art after considering the identity and amount of hydrophobic compound included in the composition. Typical emulsifying surfactants are listed in the CFTA Handbook at page 87 through 94, incorporated herein by reference.

To demonstrate the gelled or solid antiperspirant compositions of the present invention, the following nonlimiting examples were prepared. In some cases, the composition of a particular example was compared to other examples or to a present day commercial antiperspirant product for an esthetic or functional property. It was found that an antiperspirant composition of the present invention leaves essentially no white residue, i.e., leaves no visually-observable white residue. Such a result is surprising because a white residue, attributable to the solid antiperspirant compound, typically is observed after other antiperspirant composition ingredients evaporate. In addition to being nonwhitening, the present antiperspirant compositions have the added esthetic benefit of being transparent. Heretofore, transparency has been difficult to achieve in gelled or solid antiperspirant compositions because the gelling agents either interacted with the antiperspirant compound or were ineffective at a low pH of about 2 to about 6.

In accordance with another important feature of the present invention, the transparent gelled or solid antiperspirant compositions of the present invention are manufactured by simply admixing composition ingredients at a relatively low temperature. Contrary to prior methods of manufacturing gelled or solid antiperspirant compositions, the elevated temperatures needed to melt the gelling agents, and the long cooling times to provide the antiperspirant composition, are not required.

An antiperspirant composition of the present invention is prepared by introducing a portion of the carrier and the hydrophilic polymeric binder into a first vessel. The resulting mixture is mixed, mildly, at a temperature of about 20° C. to about 45° C., until homogeneous. Then, the softening agent and all other optional ingredients are added to the first vessel, in any order, and agitation is continued until the resulting mixture is homogeneous. Finally, the borate crosslinker is added to the first vessels and agitation is continued until the mixture is homogeneous. In a second vessel, the antiperspirant compound and the remaining portion of the carrier are admixed, then heated to about 40° C. to about 45° C. and stirred until homogeneous. Next, the homogeneous mixture in the first vessel is slowly added to the homogeneous solution in the second vessel. The resulting mixture is stirred until homogeneous, and the resulting solution is poured into a suitable antiperspirant container and allowed to cool to room temperature. The amount of borate crosslinker included in the antiperspirant composition determines the time required for the antiperspirant compound to solidify, and determines the firmness and brittleness of the antiperspirant composition. The antiperspirant composition is transparent unless an intentionally-added optional ingredient provides an opaque or pearlescent composition.

As will be demonstrated in the following examples, the antiperspirant compositions were transparent and phase-stable over the life of the product; were firm and nonbrittle, thereby resisting cracking and crumbling; were easy to apply and effectively delivered the antiperspirant compound to the skin; and did not whiten the skin or clothing. Each of the following examples was prepared by the above-described method.

EXAMPLES 10–14

The compositions of Examples 10–14 illustrate that the amount of borate crosslinker incorporated into the antiperspirant composition, relative to the amount of antiperspirant compound, influences the physical form, texture, brittleness, solidification temperature, and pH of the antiperspirant composition.

| Ingredients | Example 10[1] | Example 11 | Example 12 | Example 13 | Example 14 (Comparative) |
|---|---|---|---|---|---|
| Antiperspirant Compound | 22.73[2] | 24.27[2] | 25.00[2] | 23.59[2] | 25.00[11] |
| Hydrophilic Polymeric Binder[8] | 2.74 | 0.67 | 3.00 | 0.67 | — |
| Propylene Glycol[9] | 46.36 | 45.73 | 32.50 | 44.36 | 61.00 |
| Water[9] | 27.26 | 26.42 | 35.00 | 25.72 | 7.50 |
| Borate Crosslinker[10] | 0.91 | 2.91 | 4.50 | 5.66 | 6.00 |
| Fragrance | — | — | — | — | 0.50 |

[8] a hydrophilic polyurethane resin having a weight average molecular weight of about 80,000, an NCO/OH ratio of 0.73, and prepared in accordance with the method of Examples 1–5 of U. S. Pat. No. 5,000,955, incorporated herein by reference;
[9] carrier;
[10] boric acid; and
[11] aluminum zirconium glycinate (AZG) available commercially as REZAL 36GPG, from Reheis, Inc., Berkeley Heights, New Jersey, added as a 100% weight percent active material.

The composition of Example 10 was a transparent, viscous liquid (viscosity 500 cps (centipoise) and pH 3.21). The composition of Example was a transparent, very viscous liquid (viscosity-5,200 cps and pH 3.22). The increased viscosity of Example 11 reflects the increased amount of borate crosslinker, e.g., boric acid, in Example 11. The composition of Example 12, which includes a greater amount of boric acid relative to the amount of antiperspirant compound than the composition of Example 11, was a transparent liquid immediately after manufacture. The transparent liquid solidified into a transparent solid antiperspirant composition in about two hours. The composition of Example 12 was a slow-setting solid antiperspirant composition. The composition of Example 12 demonstrated excellent sensory properties when rubbed across the skin.

The composition of Example 13, including a further increased amount of boric acid, was a quick-setting solid antiperspirant composition. The composition of Example 13 initially was a transparent liquid composition that solidified into a transparent solid antiperspirant composition in about 30 minutes. The composition of Example 13 demonstrated excellent sensory properties when rubbed across the skin. The composition of Example 14 was a comparative example illustrating that a transparent, fast-setting (about 30 minutes), solid antiperspirant composition can be manufactured in the absence of a hydrophilic polymeric binder. However, the comparative composition of Example 14 was more brittle, and was more susceptible to fracturing and crumbling. The comparative composition of Example 14 also illustrated that a borate crosslinker crosslinks a different type of antiperspirant compound, i.e, AZG. All of the compositions of Examples 10–14 exhibited long term stability at room temperature, and for at least one month at 50° C.

The following Examples 15–20 demonstrate that the molecular weight of the hydrophilic polymeric binder influences the brittleness of a solid antiperspirant composition. Examples 15–20 illustrate that antiperspirant compositions comprising a hydrophilic polymeric binder are not brittle, and consequently do not crack or crumble, and effectively deliver the antiperspirant compound when rubbed against the skin. Examples 15–20 also illustrate that the nature, molecular weight and amount of hydrophilic polymeric binder influences the transparent solid antiperspirant compositions.

| Ingredients | Example 15[1] | Example 16 | Example 17 (Comparative) |
|---|---|---|---|
| Antiperspirant Compound | 20.0[2] | 20.0[2] | 20.4[2] |
| Hydrophilic Polymeric Binder[12] | 10.0 | 5.0 | — |
| Propylene Glycol[9] | 42.0 | 41.0 | 45.9 |
| Water[9] | 23.0 | 30.0 | 29.6 |
| Borate Crosslinker[10] | 5.0 | 4.0 | 4.1 |
| Properties: | Transparent; soft, non-brittle | Transparent; soft, non-brittle | Transparent; hard, brittle |

[12] a hydrophilic polyurethane resin having a weight average molecular weight of about 146,000, an NCO/OH ratio of 0.92, and prepared in accordance with the methods of Examples 1–5 of U. S. Pat. No. 5,000,955, incorporated herein by reference.

| Ingredients | Example 18[1] | Example 19 | Example 20 (Comparative) |
|---|---|---|---|
| Antiperspirant Compound | 23.58[2] | 20.8[2] | 20.0[2] |
| Hydrophilic Polymeric Binder[13] | 0.67 | 5.0 | — |
| Propylene Glycol[9] | 44.37 | 41.0 | 47.0 |
| Water[9] | 25.72 | 29.2 | 29.0 |
| Borate Crosslinker[10] | 5.66 | 4.0 | 4.0 |
| Properties: | Transparent; soft, non-brittle | Transparent; soft, non-brittle | Transparent; hard, brittle |

[13] a carboxylated hydrophilic polyurethane resin having a weight average molecular weight of about 80,000, an NCO/OH ratio of 0.73, and an acid number of 5.96 g potassium hydroxide per gram of resin, prepared in accordance with U. S. Pat. Nos. 4,255,550; 4,743,673; and, 4,156,067, each incorporated herein by reference.

The compositions of Examples 15–20 each were transparent solid antiperspirant compositions. The compositions of 15, 16, 18 and 19 were firm, nonbrittle, did not fracture or crumble under typical application conditions, and were commercially acceptable. The comparative compositions of Examples 17 and 20 did not incorporate a hydrophilic polymeric binder. The comparative compositions of Examples 17 and 20 were transparent, and were esthetically and functionally acceptable. The comparative compositions of Examples 17 and 20 exhibited an increased hardness and brittleness. The hardness and brittleness of the comparative compositions of Examples 17 and 20 make these antiperspirant compositions less commercially acceptable to particular consumers. The compositions of Examples 15–20 exhibited long term stability at room temperature, and for at least one month at 50° C.

The compositions of Examples 16 and 19 were identical except for the molecular weight of the hydrophilic polymeric binder. The composition of Example 16 incorporated a higher molecular weight hydrophilic polyurethane and exhibited less brittleness, fracturing and crumbling, but slightly more tack. These properties were attributed to the high molecular weight hydrophilic polymeric binder. Accordingly, a lesser amount of a high molecular weight polyurethane can be incorporated into the gelled or solid antiperspirant composition to provide the same benefits as a greater amount of a lower molecular weight polyurethane. The composition of Example 18 illustrated that even low amounts of the hydrophilic polymeric binder effectively reduces the hardness and brittleness of the transparent solid antiperspirant composition.

| Example 21 (comparative) | |
|---|---|
| Ingredients[1] | |
| Aluminum Chlorohydrate[2] | 20.0 |
| Boric acid | 6.0 |
| Glycerin | 24.0 |
| Water[14] | 50.0 |

[14] Carrier.

The comparative composition of Example 21 was a transparent, solid antiperspirant composition that does not incorporate a hydrophilic polymeric binder. The comparative transparent composition of Example 21 was a brittle solid having a slightly rubbery consistency. Glycerin, which typically plasticizes resins, did not reduce the brittleness of the comparative composition of Example 21. The brittleness of the comparative composition of Example 21 made the antiperspirant composition less commercially acceptable to particular consumers. Accordingly, it has been demonstrated that typical plasticizers, like polyols and esters, do not reduce the hardness and brittleness of the antiperspirant compositions. A hydrophilic polymeric binder therefore is used to provide a commercially-acceptable firm, but nonbrittle, gelled antiperspirant composition.

In addition to a hydrophilic polyurethane, other classes of hydrophilic polymeric binders can be utilized in the present antiperspirant compositions, in place of or in combination with a hydrophilic polyurethane. In addition, other carriers can be utilized in the present antiperspirant compositions. The following Examples 22–31 therefore illustrate other embodiments of the present invention.

| Ingredients | Example 22[1] (Comparative) | Example 23[1] |
|---|---|---|
| Antiperspirant Compound | 25.0[2] | 25.0[2] |
| Hydrophilic polymeric binder | 4.0[15] | 2.0[15] |
| Water[9] | 71.0 | 25.0 |
| Propylene Glycol[9] | — | 43.5 |
| Boric Acid | — | 4.5 |

[15] AMERCELL ™ Polymer HM-1500, a nonionic, water-soluble, hydrophobically-modified hydroxyethyl cellulose having a molecular weight greater than 50,000, available commercially from Amerchol Corp., Edison, NJ.

The composition of comparative Example 22 was a slightly hazy, pale yellow, flowable gel-like composition. The composition of Example 22 spread easily on the skin and dried quickly, leaving behind a film. The composition of Example 22 had a very slight tack. The composition of Example 22 was phase stable and phase reversible at 25° C., 50° C., and was stable to freeze thaw cycles.

The composition of Example 23 was a clear, pale yellow, hard solid. The composition of Example 23 incorporates a borate crosslinker, an antiperspirant compound and a hydrophilic polymeric binder in accordance with the present invention. The composition of Example 23 was a stable composition that applied to the skin easily and did not leave a white residue after drying.

The compositions of Examples 24–31 incorporate polyethylene glycols (PEG) of different molecular weights as the hydrophilic polymeric binder to reduce composition brittleness and improve composition consistency.

glycols more effectively reduced brittleness, cracking and crumbling of the compositions of Examples 24–31. Therefore, an antiperspirant composition of the present invention preferably includes a relatively high molecular weight polyethylene glycol, such as about 100,000 or greater to about 5,000,000, to more effectively reduce brittleness, fracturing and crumbling. The tack imparted to the transparent gelled antiperspirant compositions by a high molecular weight PEG can be reduced by using a lesser amount of the PEG (Example 31) or by using a combination of a high molecular weight PEG and a low molecular weight PEG. The room temperature stability of the compositions of Examples 24–31 was monitored for 5 months. The stability of each composition was good.

| Ingredients | Example 32[1] | Example 33 |
|---|---|---|
| Antiperspirant Compound | 14.6[2] | 16.7[2] |
| Hydrophilic Polymeric Binder | 2.1[24] | 1.0[24] |
| Propylene Glycol[9] | 33.8 | 40.0 |
| Water[9] | 45.2 | 37.5 |
| Borate crosslinker[10] | 3.8 | 4.3 |
| Fragrance | 0.5 | 0.5 |
| Properties: | Transparent; soft, nonbrittle | Transparent; soft, brittle |

[24] a hydrophilic polyurethane resin having a weight average molecular weight of about 248,000, an NCO/OH ratio of 0.98, and prepared in accordance with the method of Examples 1–5 of U. S. Pat. No. 5,000,955, incorporated herein by reference.

Compositions including a relatively low amount of antiperspirant compound are termed deodorants as opposed to antiperspirants. The compositions of Examples 32 and 33 illustrate transparent gelled deodorant compositions of the present invention. The compositions of Examples 32 and 33 also illustrate that the amount of hydrophilic polymeric binder effects the consistency of the composition. The composition of Example 32 was firm and nonbrittle. The composition of Example 33 was firm and brittle. Accordingly, a sufficient amount of hydrophilic polymeric binder is present in the antiperspirant composition for a given amount

| Ingredients | Example 24[1] | Example 25) | Example 26 | Example 27 | Example 28 | Example 29 | Example 30 | Example 31 |
|---|---|---|---|---|---|---|---|---|
| Antiperspirant Compound | 22.0[2] | 22.0[2] | 22.0[2] | 22.0[2] | 22.0[2] | 22.0[2] | 22.0[2] | 22.0[2] |
| Propylene Glycol[9] | 45.9 | 45.9 | 45.9 | 44.4 | 44.4 | 44.4 | 44.4 | 46.15 |
| Ethanol[9] | 5.0 | 5.0 | 5.0 | 5.0 | 5.0 | 5.0 | 0 | 5.0 |
| Water[9] | 22.0 | 22.0 | 22.0 | 22.0 | 22.0 | 22.0 | 22.0 | 22.0 |
| Borate Crosslinker[10] | 4.6 | 4.6 | 4.6 | 4.6 | 4.6 | 4.6 | 4.6 | 4.6 |
| Hydrophilic Polymeric Binder | 0.5[16] | 0.5[17] | 0.5[18] | 2.0[19] | 2.0[20] | 2.0[21] | 2.0[22] | 0.25[23] |

[16] PEG 350, molecular weight about 15,000;
[17] PEG 2M, molecular weight about 100,000;
[18] PEG 5M, molecular weight about 200,000;
[19] PEG 7M, molecular weight about 300,000;
[20] PEG 14M, molecular weight about 600,000;
[21] PEG 23M, molecular weight about 1,000,000;
[22] PEG 45M, molecular weight about 2,000,000; and
[23] PEG 90M, molecular weight about 4,000,000.

The compositions of Examples 24–31 were transparent antiperspirant solids having excellent firmness; were nonbrittle and had excellent esthetic and functional properties. The tack of the compositions of Examples 24–31 increased with the increasing molecular weight of the polyethylene glycols. However, the higher molecular weight polyethylene of borate crosslinker to provide a firm, but nonbrittle composition. The necessary amount of hydrophilic polymeric binder varies both with the amount of borate crosslinker in the composition and the identity of the hydrophilic polymeric binder. For example, 1% by weight of hydrophilic binder in Example 33 was an insufficient amount for 4.3% boric acid, whereas 0.25% by weight hydrophilic polymeric binder in Example 31 was sufficient for 4.6% boric acid.

A sufficient amount of hydrophilic polymeric binder is present in the antiperspirant composition if the composition has a penetrometer value in the range of about 4 to about 10 mm (millimeter). Below a penetrometer value of about 4 mm, the antiperspirant composition is too brittle and has a tendency to fracture and crumble. Above a penetrometer value of value of about 10 mm, the antiperspirant composition is too soft and has a tendency to flow. Preferably, the present antiperspirant compositions have a penetrometer value of about 5 to about 10 mm.

An important feature of the present invention is reduction of the white residue on skin and clothing resulting from the use of an antiperspirant composition. The absence of a white residue is a primary esthetic property desired by consumers in antiperspirant compositions.

Roll-on antiperspirants and present-day compressed powder stick antiperspirants leave a cosmetically-unacceptable white residue on the skin or clothing after application to the skin. The examples of the present invention demonstrate that incorporating a hydrophilic polymeric binder in gelled or solid antiperspirant compositions reduces brittleness and crumbling of the composition, and also reduces the white residue on skin and clothing. The antiperspirant compositions of the present invention did not leave a visually observable residue on the skin, and did not stain clothing after drying.

The compositions of Examples 34–36 were identical, except 1% by weight of a hydrophilic polyurethane resin, having a weight average molecular weight of about 248,000 and an NCO/OH ratio of 0.98, was incorporated into the compositions of Examples 35 and 36, and further 1% of a borate crosslinker (boric acid) was incorporated into the composition of Example 36. Examples 34 and 35 are comparative examples.

| Ingredients | Example 34[1] (comparative) | Example 35 (comparative) | Example 36 |
|---|---|---|---|
| Antiperspirant Compound | 25.0[28] | 25.0[28] | 25.0[28] |
| Hydrophilic Polymeric Binder | — | 1.0[24] | 1.0[24] |
| Carrier | 75.0[25] | 74.0[26] | 73.0[27] |
| Borate Crosslinker | — | — | 1.0[10] |

[25] 70% propylene carbonate and 5% hexylene glycol;
[26] 69% propylene carbonate and 5% hexylene glycol;
[27] 68% propylene carbonate and 5% hexylene glycol; and
[28] ACH Powder 323, an impalpable aluminum chlorohydrate, available from Dow Corning Corp. Midland, MI, added as a 100% active material.

The compositions of Examples 34–36 were tested for whitening by individually applying 0.5 ml (milliliter) of each composition to a blackboard. Each composition was spread evenly on the blackboard with a doctor blade. The white residue left by the compositions of Examples 35–36 was observed visually. The white residue left by the compositions of Examples 34 and 35 was measured at 30 minutes and at 2 hours after application with a chromameter.

The visual tests showed that the compositions of Examples 35 and 36 performed equally with respect leaving essentially no white residue on the skin. The chromameter tests showed that after 30 minutes the composition of Example 34 left less of a white residue than the composition of Example 35. After two hours, the composition of Example 35 left no visually observable white residue on the skin.

Therefore, the comparative composition of Example 34, which does not include a hydrophilic polymeric binder, left the greatest amount of white residue 2 hours after application. The compositions of Examples 35 and 36, incorporating a polymeric binder, left a substantially lower white residue. After two hours of drying, the compositions of Example 36, incorporating a borate crosslinker, performed as well as the comparative composition of Example 35. The borate crosslinker therefore did not contribute to whitening of the skin or clothing.

The following Examples 37–41 illustrate antiperspirant compositions of the present invention incorporating a softening agent. The softening agent improves the ability of the transparent, gelled or solid antiperspirant composition to deliver the antiperspirant compound to the skin.

Example 37

| Ingredients | % (by weight)[1] |
|---|---|
| Aluminum chlorohydrate[2] | 25 |
| Borate crosslinker[10] | 4 |
| Propylene glycol[9] | 33 |
| Water[9] | 34 |
| Hydrophilic polymeric Binder[8] | 2 |
| Softening agent[29] | 2 |

[29] a polyoxyethylene glyceride ester (PEG 200 Castor Oil), having an HLB of 18.1 available from ICI Americas Inc., Wilmington, DE, under the brand name ATLAS G-1300.

The composition of Example 37 was a transparent gelled solid having excellent esthetic and functional properties, including an improved ability to deliver the antiperspirant compound to the skin in comparison to the composition of Example 12. The composition of Example 12 is almost identical to the composition of Example 37, but the composition of Example 12 does not include a softening agent.

The presence or absence of a hydrophilic polymeric binder does not appreciably affect the transparency of the antiperspirant composition. The compositions of Examples 38 and 39 therefore demonstrate that a judicious selection of the amount and identity of the softening agent maintains the transparency of the antiperspirant composition. The determination of the identity and amount of softening agent necessary to maintain composition transparency is readily determined by a person skilled in the art.

| Ingredients | Example 38[1] | Example 39 |
|---|---|---|
| Aluminum chlorohydrate[2] | 25.42 | 26.79 |
| Borate crosslinker[10] | 4.23 | 4.46 |
| Propylene glycol[9] | 29.66 | 31.37 |
| Water[9] | 29.51 | 31.06 |
| Oleth-10 (HLB = 12.4)[30] | 1.86 | 1.86 |
| Polysorbate-20 (HLB = 16.7)[30] | 9.32 | 4.46 |
| Appearance | Transparent stick | Hazy stick |

Example 40

| Ingredients | % (by weight)[1] |
|---|---|
| Aluminum chlorohydrate[2] | 20.0 |
| Borate crosslinker[31] | 3.0 |
| Water[9] | 44.9 |
| Propylene glycol[9] | 30.0 |

| | |
|---|---|
| Hydrophilic Polymeric Binder[24)] | 0.1 |
| Softening agent[32)] | 2.0 |

[30)]Softening agents.
[31)]borax; and
[32)]methyl gluceth-20.

The composition of Example 40 incorporated borax (sodium tetraborate) as the borate crosslinking agent. The composition of Example 40 was a transparent solid having excellent phase stability, esthetic properties and functional properties. The composition of Example 41 incorporated a dimethicone copolyol as the softening agent. The composition of Example 41 was a transparent gelled antiperspirant composition having good esthetic properties.

Example 41

| Ingredients | % (by weight)[1)] |
|---|---|
| Aluminum chlorohydrate[2)] | 20.0 |
| Borate crosslinker[10)] | 4.0 |
| Water[9)] | 20.0 |
| Propylene glycol[9)] | 45.5 |
| Hydrophilic Polymeric binder [12)] | 0.5 |
| Softening agent[33)] | 10.0 |

[33)]Dimethicone copolyol, available commercially as DOW CORNING 190 POLYETHER, Dow Corning Corporation, Midland, MI.

The compositions of Examples 37–41 were single phase compositions incorporating water-soluble and water-dispersible ingredients. In accordance with an important feature of the present invention, the transparent gelled antiperspirant compositions also can incorporate an emulsified hydrophobic compound and maintain composition transparency, efficacy and esthetics. Such antiperspirant compositions therefore include a polar phase, an oil phase and at least one emulsifier. The polar phase comprises the antiperspirant compound, water, propylene glycol, other hydrophilic carriers, the hydrophilic polymeric binder, the borate crosslinker and any other water-soluble or water-dispersible optional ingredients, including the softening agent.

The oil phase includes the hydrophobic compound, such as, for example, hydrocarbon oils, volatile and nonvolatile hydrocarbon fluids, volatile cyclic dimethylsiloxanes, volatile and nonvolatile linear dimethylsiloxanes, waxes, and saturated and unsaturated oils and fats, and water-insoluble emollients, such as fatty ($C_8$–$C_{22}$) alcohols. The oil phase conventionally includes volatile or low viscosity hydrocarbon fluids, volatile dimethylsiloxanes and mixtures thereof. The main purpose of the oil phase is to provide enhanced esthetic properties, such as emolliency, slip during application over the skin, and an improved perception of dryness, to increase consumer acceptance of the composition.

The oil phase is insoluble in water and therefore is emulsified, preferably with a nonionic emulsifier. Anionic and cationic emulsifiers have the ability to interact with the antiperspirant compound or the borate crosslinker, and thereby reduce composition stability and efficacy. Especially, preferred emulsifiers are nonionic surfactants, or blends thereof, having a hydrophilic-lipophilic balance (HLB) of about 2 to about 18. Particularly preferred emulsifiers are ethoxylated and/or propoxylated fatty ($C_4$ to $C_{22}$) alcohols and mixtures thereof.

Examples 42 through 58, illustrated below and in Table 1, are solid antiperspirant compositions prepared using various levels of boric acid as the borate crosslinker, laureth-4 as an emulsifier, and the hydrocarbon oil 1-decene dimer, as the hydrophobic component. The weight percent of ingredients numbered 1 to 7 was maintained constant in the compositions of Examples 42–58. The compositions were adjusted to 100% wt. by adding propylene glycol as a carrier.

| | Ingredient | % (by weight)[1)] |
|---|---|---|
| 1 | Aluminum chlorohydrate[2)] | 20.0 |
| 2 | Water 9) | 20.0 |
| 3 | Steareth-20 (HLB-15.3)[30)] | 2.5 |
| 4 | PPG-11 stearyl ether[37)] | 3.0 |
| 5 | Isohexadecane[36)] | 4.0 |
| 6 | Hydrophilic Polymeric binder[34)] | 0.1 |
| 7 | Fragrance | 0.5 |
| 8 | Laureth-4 (HLB = 9.4)[35)] | 5.98 to 16.0 according to Table 1 |
| 9 | 1-Decene Dimer[36)] | 0 to 10.0 according to Table 1 |
| 10 | Boric acid | 3.16 to 4.84 according to Table 1 |
| 11 | Porpylene glycol[9)] | q.s |

[34)]a hydrophilic polyurethane having a weight average molecular of about 146,000, an NCO/OH ratio of 0.92, and prepared in accordance with the method of Examples 1–5 of U. S. Pat. No. 5,000,955, incorporated herein by reference;
[35)]emulsifier, available commercially from ICI Americas, Inc., Wilmington, DE, as BRIJ 30;
[36)]hydrophobic compound, available commercially from Ethyl Corp., Baton Rouge, LA, as ETHYL FLOW 362; and
[37)]softening agent, available commercially from ICI America, Inc., Wilmington, DE, as ARLAMOL F.

The compositions of Examples 42 through 58 were prepared by admixing ingredients numbered 3, 4, 6, 8 and 11 in a first vessel to obtain a homogeneous solution. Then, ingredients 5, 7 and 9 were added to the homogeneous solution. Stirring was continued until the solution again was homogeneous. Then, ingredient 10 was added to the solution. The resulting mixture again was stirred until a homogeneous mixture was formed. Ingredients 1 and 2 were admixed in a second vessel to form a solution. The homogeneous mixture in the first vessel was added to the solution in the second vessel with constant stirring until a homogeneous composition resulted. The homogeneous composition was cast into antiperspirant containers and allowed to set.

The resulting transparent solid antiperspirant compositions of Examples 42 through 58 were evaluated subjectively for hardness, tack, transparency, brittleness and payoff (ability to deliver the antiperspirant compound). The transparency of the antiperspirant compositions was determined spectrophotometrically by measuring % transmittance at 700 nm (nanometers), using water as the standard for 100% transmittance. The results of the evaluations are tabulated in Table 1. In the evaluations, each stick was evaluated subjectively by two individuals and the results were averaged. The ranking schedule used by the judges was:

Brittleness:

very brittle=5 (breaks by itself), brittle=4, medium brittleness=3, slightly brittle=2, non-brittle=1;

Hardness:

very hard=5 (rock like), hard=4, medium hardness=3, soft=2, very soft=1; the hardness scale is subjective but semiquantitively correlates to a penetrometer reading (ASTM D5-86) as follows: very hard=less than 4 mm, hard=4–6 mm, medium hard=6–8 mm, soft=8–10 mm, very soft=greater than 10 mm;

Tack:

no tack=3, tacky=2, very tacky (glue like)=1;

Pay-off:
 no pay-off=5, some pay-off=4, pays-off=3, good pay-off=2, too much pay-off=1;
Transparency:
 milky=1, opaque=2, hazy=3, slightly hazy=4, water clear=5; transmittance % measured a 700 nm.

TABLE 1

SOLID ANTIPERSPIRANT COMPOSITIONS CONTAINING EMULSIFIED HYDROPHOBIC COMPOUNDS

| Example | Laureth-4 (Emulsifier) (% wt.) | Boric Acid (% wt.) | 1-Decene Dimer (% wt.) | Brittleness | Hardness | Tack | Transparency (Transmittance %) | Pay off |
|---|---|---|---|---|---|---|---|---|
| 42 | 14 | 4.5 | 2.0 | 2 | 3 | 2 | 3 (53.5) | 4 |
| 43 | 14 | 3.5 | 8.0 | 3 | 2 | 2 | 4 (77.0) | 4 |
| 44 | 11 | 4.0 | 5.0 | 4 | 4 | 3 | 4 (90.0) | 1 |
| 45 | 8 | 3.5 | 2.0 | 4 | 2 | 2 | 4 (99.6) | 2 |
| 46 | 8 | 4.5 | 8.0 | 4 | 4 | 3 | 3 (60.0) | 1 |
| 47 | 8 | 4.5 | 2.0 | 4 | 4 | 3 | 4 (94.0) | 1 |
| 48 | 8 | 3.5 | 8.0 | 4 | 3 | 2 | 3 (72.0) | 3 |
| 49 | 11 | 4.0 | 5.0 | 4 | 4 | 3 | 4 (89.0) | 2 |
| 50 | 14 | 4.5 | 8.0 | 2 | 3 | 2 | 3 (83.0) | 4 |
| 51 | 14 | 3.5 | 2.0 | 1 | 2 | 2 | 4 (80.0) | 4 |
| 52 | 5.98 | 4.0 | 5.0 | 3 | 4 | 3 | 2 (45.5) | 1 |
| 53 | 11 | 4.84 | 5.0 | 2 | 5 | 3 | 4 (94.0) | 2 |
| 54 | 11 | 4.0 | — | 3 | 3 | 2 | 5 (99.0) | 2 |
| 55 | 11 | 4.0 | 5.0 | 3 | 4 | 3 | 4 (89.0) | 1 |
| 56 | 11 | 3.16 | 5.0 | 2 | 1 | 1 | 4 (97.0) | 5 |
| 57 | 11 | 4.0 | 10.0 | 4 | 4 | 3 | 3 (90.0) | 1 |
| 58 | 16 | 4.0 | 5.0 | 1 | 2 | 3 | 3 (60.0) | 4 |

The results tabulated in Table 1 show that transparent solid antiperspirant compositions of the present invention including emulsified hydrophobic components can be prepared. By a judicious choice of ingredients, the transparent gelled or solid antiperspirant compositions demonstrate excellent esthetic and functional properties, such as transparency, pay-off, nonbrittleness, firmness and low tack. In addition, the compositions leave no visually-observable white residue on skin or clothing. The compositions of Examples 42–58 exhibited an excellent stability at room temperature.

Examples 59 through 74, illustrated below and in Table 2, are solid antiperspirant compositions prepared using a volatile hydrocarbon, like isodecane, as the hydrophobic component. The compositions of Examples 59 through 74 demonstrate that by varying the amount of antiperspirant compound, hydrophilic polymeric binder, emulsifier and/or carrier, a range of solid antiperspirant hardness and brittleness can be attained. However, the relationship between amounts of a particular ingredient included in the antiperspirant compound and the hardness and brittleness of the antiperspirant composition is empirical. Therefore, a person skilled in the art of formulating antiperspirant compositions can design an antiperspirant composition of desired hardness and brittleness by a judicious selection of specific composition ingredients and the amount of each ingredient.

| | Ingredient | % (by weight)[1] |
|---|---|---|
| 1 | Aluminum chlorohydrate[2] | 20 to 22.5 |
| 2 | Laureth-4 (HLB = 9.4)[35] | 8 to 15 |
| 3 | Steareth-20 (HLB = 15.3)[37] | 2.5 |
| 4 | PPG-11 stearyl ether[38] | 3.0 |
| 5 | Boric Acid | 4.5 |
| 6 | Hydrophilic Polymeric Binder[38] | 0.5 to 1.0 |
| 7 | Isodecane[39] | 10.0 |
| 8 | Propylene glycol[9] | q.s. |
| 9 | Water | 29 to 32 |

[38] a hydrophilic polyurethane having a weight average molecular of about 146,000, an NCO/OH ratio of 0.92, and prepared in accordance with the method of Examples 1–5 of U. S. Pat. No. 5,000,955, incorporated herein by reference; and
[39] volatile hydrocarbon available commercially from Presperse, Inc., South Plainfield, NJ, as a 100% active material.

The compositions of Examples 59 through 74 were prepared by a method similar to the method of preparing the compositions of Examples 42 through 58. The solid antiperspirant compositions of Examples 59 through 74 were tested for hardness using a penetrometer in accordance with ASTM Method D5-86. The hardness values are tabulated in Table 2. Table 2 also illustrates brittleness, clarity and pay-off, wherein each term has the definition set forth in Table 1.

TABLE 2

VARIATION OF SOLID ANTIPERSPIRANT COMPOSITION BRITTLENESS, CLARITY, HARDNESS AND PAY OFF WITH FORMULATION COMPOSITION

| Example | Aluminum Chlorohydrate (% wt.) | Laureth-4 (% wt.) | Hydrophilic Polymeric Binder (% wt.) | Brittleness | Clarity | Hardness (mm) | Pay off |
|---------|-------------------------------|-------------------|--------------------------------------|-------------|---------|---------------|---------|
| 59 | 21.5 | 11.5 | 0.75 | 2 | 5 | 9.03 | 4 |
| 60 | 20.0 | 8.0 | 0.50 | 3 | 5 | 5.46 | 4 |
| 61 | 22.5 | 8.0 | 0.50 | 5 | 5 | 7.40 | 5 |
| 62 | 21.25 | 8.0 | 0.75 | 3 | 5 | 9.96 | 2 |
| 63 | 20.0 | 15.0 | 1.00 | 2 | 4 | 8.50 | 2 |
| 64 | 22.5 | 15.0 | 1.00 | 4 | 4 | 6.35 | 4 |
| 65 | 22.5 | 15.0 | 0.50 | 5 | 5 | 6.60 | 4 |
| 66 | 22.5 | 11.5 | 0.75 | 4 | 5 | 5.90 | 4 |
| 67 | 21.25 | 11.5 | 1.00 | 2 | 5 | 8.90 | 3 |
| 68 | 22.5 | 8.0 | 1.00 | 2 | 5 | 8.43 | 2 |
| 69 | 21.25 | 15.0 | 0.75 | 2 | 5 | 7.43 | 4 |
| 70 | 20.0 | 11.5 | 0.75 | 3 | 5 | 7.96 | 2 |
| 71 | 21.25 | 11.5 | 0.50 | 2 | 5 | 7.80 | 4 |
| 72 | 20.0 | 8.0 | 1.00 | 4 | 5 | 7.50 | 4 |
| 73 | 20.0 | 15.0 | 0.50 | 3 | 5 | 8.73 | 4 |
| 74 | 21.25 | 11.5 | 0.75 | 2 | 5 | 9.03 | 4 |

The results tabulated in Table 2 show the relative hardness of antiperspirant compositions of the present invention. The compositions of Examples 59 through 74 have a hardness value of 5.46 through 9.96 mm (millimeters). This range of hardness values compares favorably with present-day commercial solid antiperspirant compositions, such as LADIES CHOICE ANTIPERSPIRANT AND DEODORANT, Carter Wallace Co., New York, N.Y. (8.0–10.00 mm), ARRID X-DRY SOLID, Carter Wallace Co., New York, N.Y. (6.6–7.8 mm), DEGREE ANTIPERSPIRANT, Helene Curtis, Inc., Chicago, Ill., (6.4–7.8 mm) and LADY SPEED STICK, The Mennen Co., Morriston, N.J. (8.4–9.1 mm).

The following Examples 75–81 illustrate further embodiments of the present invention. The compositions of Examples 75–81 each were solid, transparent compositions having good esthetic properties and an excellent ability to deliver the antiperspirant compound to the skin. The compositions of Examples 75–81 did not leave a visually-observable white residue on skin or clothing, were firm, were nonbrittle and resisted fracturing and crumbling.

Example 75

| Ingredients | % (by weight)[1] |
|-------------|------------------|
| Antiperspirant compound[2] | 22.0 |
| Propylene glycol[9] | 38.9 |
| Water[9] | 22.0 |
| Ethanol[9] | 5.0 |
| Dimethicone copolyol[32] | 5.0 |
| Borate Crosslinker[10] | 4.6 |
| Polyethylene glycol[19] | 2.0 |
| Fragrance | 0.5 |

Example 76

| Ingredients | % (by weight)[1] |
|-------------|------------------|
| Antiperspirant compound[2] | 22.0 |
| Propylene glycol[9] | 37.9 |
| Water[9] | 22.0 |
| Ethanol[9] | 5.0 |
| Dimethicone copolyol[32] | 5.0 |
| Emulsifier[29] | 1.0 |
| Borate Crosslinker[10] | 4.6 |
| Polyethylene glycol[19] | 2.0 |
| Fragrance | 0.5 |

Example 77

| Ingredients | % (by weight)[1] |
|-------------|------------------|
| Antiperspirant compound[2] | 22.0 |
| Propylene glycol[9] | 25.9 |
| Water[9] | 22.0 |
| Ethanol[9] | 5.0 |
| Borate Crosslinker[10] | 4.6 |
| Polyethylene glycol[19] | 2.0 |
| Fragrance | 0.5 |
| C$_{12-15}$ Alkyl Benzoate[30] | 2.0 |
| PPG-5-Ceteth-20[29] | 10.0 |

Example 78

| Ingredients | % (by weight)[1] |
|-------------|------------------|
| Antiperspirant compound[2] | 22.0 |
| Propylene glycol[9] | 37.9 |
| Water[9] | 22.0 |
| Ethanol[9] | 5.0 |
| Borate Crosslinker[10] | 4.6 |
| Polyethylene glycol[19] | 2.0 |
| Fragrance | 0.5 |
| C$_{12-15}$ Alkyl | 1.0 |

Example 78 -continued

| Ingredients | % (by weight)[1] |
|---|---|
| Benzoate[29] Laureth-4[35] | 5.0 |

Example 79

| Ingredients | % (by weight) |
|---|---|
| (Phase I) | |
| Antiperspirant compound[2] | 21.5 |
| Glycerin[9] | 16.5 |
| Waterp[9] | 33.0 |
| Borate Crosslinker[10] | 4.5 |
| (Phase II) | |
| AMERSIL ME-358[40] | 21.0 |
| ABIL ® EM-90[41] | 3.0 |
| Fragrance | 0.5 |

[40] a blend of cyclomethicone and dimethicone copolyol, available from Amerchol Corp., Edison, NJ; and
[41] cetyl dimethicone copolyol, available from Goldschmidt Chemical Corp., Hopewell, VA.

Example 80

| Ingredients | % (by weight) |
|---|---|
| (Phase I) | |
| Antiperspirant compound[2] | 19.33 |
| Dipropylene Glycol[9] | 19.32 |
| Water[9] | 33.23 |
| Borate Crosslinker[10] | 3.38 |
| (Phase II) | |
| AMERSIL ME-358[40] | 21.26 |
| Fragrance | 0.48 |

The compositions of Examples 79 and 80 were prepared by admixing all ingredients of phase I, except the antiperspirant compound, in a vessel at room temperature. The antiperspirant compound was added to phase I after the borate crosslinker was completely dissolved. Optionally, heating the mixture of phase I ingredients to about 50°–60° C. decreases the time to dissolve the borate crosslinker.

Independently, the ingredients of phase II were admixed at room temperature. Then, phase I was added to phase II with agitation. The resulting solution was very viscous, and was cast into antiperspirant canisters and allowed to set. In each of Examples 79 and 80, the resulting antiperspirant sticks were clear, nonbrittle and moderately hard. The composition of Example 79 had a greater clarity than the composition of Example 80. Both antiperspirant sticks had good tactile properties. Compositions identical to Examples 79 and 80, except for excluding boric acid, were very soft gels.

Example 81

| Ingredients | % (by weight) |
|---|---|
| Antiperspirant compound[42] | 19.0 |
| Hydrophilic Polymeric Binder[19] | 0.3 |
| Propylene glycol[9] | 36.0 |
| Water[9] | 40.7 |
| Borate Crosslinker[10] | 4.0 |

[42] a blend of 10% by weight CHLOROHYDROL, added as a 50% by weight solution of ACH in water, and 9% by weight Aluminum Zirconium tetrachlorohydrex-PG, available commercially as REACH AZP 908PG, from Reheis, Inc., Berkley Heights, New Jersey, added as a 30% by weight solution of aluminum zirconium tetrachlorohydrex-PG in propylene glycol.

The composition of Example 81, containing a combination of antiperspirant compounds, was a clear solid that delivered a good payoff upon application to the skin. The composition of Example 81 was prepared by adding a solution of the hydrophilic polymeric binder, propylene glycol, water and borate crosslinker to the antiperspirant compound at a temperature of about 50° C., then stirring the mixture until homogeneous and allowed to cool at room temperature in an antiperspirant container.

The transparent antiperspirant compositions of the present invention exhibit unique and superior properties upon topical application to skin. The improved physical and sensory properties include a firm, but nonbrittle, consistency to effectively deliver the antiperspirant compound to the skin; storage stability; elimination of the shaking requirement to redistribute the antiperspirant compound prior to use; essentially no whitening of the skin and clothing after topical application; and transparency for enhanced consumer acceptance.

It should be understood that the foregoing detailed description is given merely by way of illustration. Obviously, many modifications and variations of the invention as hereinbefore set forth can be made without departing from the spirit and scope thereof and therefore only such limitations should be imposed as are indicated by the appended claims.

What is claimed and desired to be secured by Letters Patent is:

1. A gelled or solid antiperspirant composition comprising:
   (a) about 1% to about 40% by weight of an antiperspirant compound;
   (b) about 0.5% to about 10% by weight of a borate crosslinker;
   (c) about 0.005% to about 10% by weight of a hydrophilic polymeric binder selected from the group consisting of a polyethylene glycol having a weight average molecular weight of at least about 5,000; and
   (d) a carrier comprising water, a water-soluble solvent and mixtures thereof;
   wherein the antiperspirant composition has a pH of about 2 to about 6.

2. The antiperspirant composition of claim 1 further comprising:
   (e) 0% to about 15% by weight of a softening agent having an HLB value of at least about 6, a weight average molecular weight of less than about 10,000, and selected from the group consisting of a polyoxyethylene ether of a fatty ($C_6$–$C_{22}$) alcohol, a polyoxypropylene ether of a fatty ($C_6$–$C_{22}$) alcohol, a dimethicone copolyol, a polypropylene glycol, an ethoxylated alkylphenol, a polyethylene glycol ether of methyl glucose, and mixture thereof.

3. The antiperspirant composition of claim 1 further comprising 0% to about 10% by weight of a hydrophobic compound selected from the group consisting of an aliphatic hydrocarbon, a fatty ($C_8$–$C_{22}$) alcohol, a siloxane, and mixtures thereof, wherein the hydrophobic compound is emulsified by an emulsifying surfactant.

4. The antiperspirant composition of claim 1 having a penetrometer reading of about 4 mm to about 10 mm.

5. The antiperspirant composition of claim 1 wherein the composition is a nonflowable and capable of maintaining a shape in the free form at room temperature for at least one day.

6. The antiperspirant composition of claim 1 wherein the composition has a % transmittance at 700 nm of at least 50%.

7. The antiperspirant composition of claim 1 wherein the antiperspirant compound is present in an amount of about 5% to about 30% by weight of the composition.

8. The antiperspirant composition of claim 1 wherein the antiperspirant compound is present in an amount of about 10% to about 25% by weight of the composition.

9. The antiperspirant composition of claim 1 wherein the antiperspirant compound is an astringent salt comprising aluminum, zirconium, zinc or a mixture thereof.

10. The antiperspirant composition of claim 1 wherein the antiperspirant compound is selected from the group consisting of aluminum chlorohydrate, aluminum bromohydrate, potassium alum, sodium aluminum chlorohydroxy lactate, aluminum-zirconium tetrachlorohydrate, an aluminum-zirconium polychlorohydrate complexed with glycine, aluminum-zirconium trichlorohydrate, aluminum-zirconium octachlorohydrate, aluminum sesquichlorohydrate, aluminum sesquichlorohydrex PG, aluminum chlorohydrex PEG, aluminum zirconium octachlorohydrex glycine complex, aluminum zirconium pentachlorohydrex glycine complex, aluminum zirconium tetrachlorohydrex glycine complex, aluminum zirconium trichlorohydrex glycine complex, aluminum chlorohydrex PG, zirconium chlorohydrate, aluminum dichlorohydrate, aluminum dichlorohydrex PEG, aluminum dichlorohydrex PG, aluminum sesquichlorohydrex PG, aluminum chloride, aluminum zirconium pentachlorohydrate, and mixtures thereof.

11. The composition of claim 1 wherein the borate crosslinker is present in an amount of about 1% to about 7% by weight of the composition.

12. The composition of claim 1 wherein the borate crosslinker is present in an amount of about 3% to about 6% by weight of the composition.

13. The composition of claim 1 wherein the borate crosslinker is selected from the group consisting of boric acid, sodium borate, sodium tetraborate, sodium metaborate, boron oxide, an oligomer of boric acid, potassium pentaborate, potassium metaborate, sodium triborate, metaboric acid, ammonium hydrogen tetraborate, magnesium borate, barium metaborate, calcium metaborate, orthoboric acid, lithium metaborate, lithium tetraborate, zirconium metaborate, and mixtures thereof.

14. The composition of claim 1 having a pH of about 3 to about 5.

15. The antiperspirant composition of claim 1 wherein the hydrophilic polymeric binder is present in an amount of about 0.01% to about 5% by weight of the composition.

16. The antiperspirant composition of claim 1 wherein the hydrophilic polymeric binder is present in an amount of about 0.1% to about 3% by weight of the composition.

17. The antiperspirant composition of claim 1 wherein the hydrophilic polymeric binder has a weight average molecular weight of about 5,000 to about 5,000,000.

18. The composition of claim 1 wherein the hydrophilic polymeric binder comprises a polyethylene glycol having a weight average molecular weight of about 15,000 to about 5,000,000.

19. The composition of claim 18 wherein the polyethylene glycol has a molecular weight of about 100,000 to about 4,000,000.

20. The composition of claim 1 wherein the carrier is selected from the group consisting of water, ethylene glycol, propylene glycol, butylene glycol, propylene carbonate, dimethyl isosorbide, hexylene glycol, ethanol, n-butyl alcohol, n-propyl alcohol, isopropyl alcohol, and mixtures thereof.

21. The composition of claim 2 wherein the softening agent is selected from the group consisting of methyl gluceth-20, methyl gluceth-10, a $C_{12-15}$ alkyl benzoate, PEG-20 methyl glucose distearate, PEG-20 methyl glucose sesquistearate, PEG-200 castor oil, PEG-6, PEG-8, $Cl_{1-15}$ pareth-20, nonoxynol-9, octoxynol-10, nonyl nonoxynol-10, ceteth-8, ceteth-12, dodoxynol-12, laureth-15, PEG-20, PEG-3 castor oil, PEG-8 castor oil, PEG-20 castor oil, poloxamer 101, polysorbate 20, PPG-11 stearyl ether, dimethicone copolyol, steareth-20, and mixtures thereof.

22. The antiperspirant composition of claim 3 wherein the hydrophobic compound is an aliphatic hydrocarbon selected from the group consisting of isohexadecane, 1-decene dimer, a mineral oil, a nonvolatile hydrocarbon fluids, and a hydrocarbon depicted by general structural formula

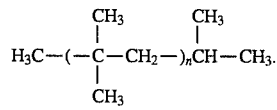

23. The antiperspirant composition of claim 3 wherein the hydrophobic compound is selected from the group consisting of a cyclic volatile siloxane, a linear volatile silioxane, a linear nonvolatile siloxane, a methicone, a phenyltrimethicone, tributoxypropyltrisiloxane, bisphenylhexamethicone, and mixtures thereof.

24. The antiperspirant composition of claim 3 wherein the emulsifying surfactant is a nonionic surfactant having a HLB value of about 2 to about 18.

25. A gelled or solid antiperspirant composition comprising:
 (a) about 5% to about 30% by weight of an aluminum halide, an aluminum hydroxyhalide, a zirconyl oxyhalide, a zirconyl hydroxyhalide, an aluminum zirconium glycinate, or a mixture thereof;
 (b) about 1% to about 7% by weight of boric acid, sodium tetraborate, or a mixture thereof;
 (c) about 0.01% to about 5% by weight of a hydrophilic polymeric binder selected from the group consisting of a polyethylene glycol having a weight average molecular weight of about 15,000 to about 4,000,000, and mixture thereof;
 (d) a carrier selected from the group consisting of water, propylene glycol, ethanol, and mixtures thereof.

26. The composition of claim 25 further comprising:
 (e) 0% to about 12% by weight of a softening agent selected from the group consisting of methyl gluceth-20, methyl gluceth-10, a $C_{12-15}$ alkyl benzoates, PEG-20 methyl glucose distearate, PEG-20 methyl glucose sesquistearate, PEG-200 castor oil, PEG-6, PEG-8, $C_{11-15}$ pareth-20, nonoxynol-9, octoxynol-10, nonyl nonoxynol-10, ceteth-8, ceteth-12, dodoxynol-12, laureth-15, PEG-20, PEG-3 castor oil, PEG-8 castor oil, PEG-20 castor oil, poloxamer 101, polysorbate 20, PPG-11 stearyl ether, dimethicone copolyol, steareth-20, and mixtures thereof.

27. The composition of claim 25 further comprising 0% to about 10% by weight of a hydrophobic compound selected from the group consisting of a volatile cyclic siloxane, a volatile linear siloxane, a nonvolatile linear siloxane, isohexadecane, 1-decene dimer, a volatile hydrocarbon having the formula

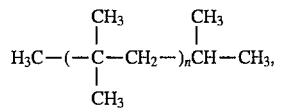

wherein n ranges from 2 to 5, and mixtures thereof.

28. A method of treating or preventing malodors associated with human perspiration comprising topically applying an effective amount of an antiperspirant composition to human skin, said composition comprising:

(a) about 1% to about 40% by weight of an antiperspirant compound;

(b) about 0.5% to about 10% by weight of a borate crosslinker;

(c) about 0.005% to about 10% by weight of a hydrophilic polymeric binder selected from the group consisting of a polyethylene glycol having a weight average molecular weight of at least about 5,000; and (d) a carrier comprising water, a water-soluble solvent and mixture thereof;

wherein the antiperspirant composition has a pH of about 2 to about 6.

29. The method of claim 28 wherein the human skin having the antiperspirant composition applied thereon has no visually-observable white residue.

* * * * *

UNITED STATES PATENT AND TRADEMARK OFFICE
CERTIFICATE OF CORRECTION

PATENT NO.   : 5,549,887
DATED        : August 27, 1996
INVENTOR(S)  : Ramiro Galleguillos et al.

It is certified that error appears in the above-identified patent and that said Letters Patent is hereby corrected as shown below:

Column 6, lines 60-61, "a antiperspirant" should be --an antiperspirant--.

Column 6, line 64, "tog" should be --to,--.

Columns 7, 8, in the table, column headed "Example 1," 2nd line, "$25^{1)}$" should be --$25^{2)}$--.

Columns 7, 8, in the table, column headed "Example 1," 8th line, "fl uid" should be --fluid--.

Column 14, line 12, "vessels" should be --vessel,--.

Column 14, last line, between "Example" and "was" insert --11--.

Columns 17, 18 (the large table spanning both columns), third row under "Example 30," "0" should be --5.0---.

UNITED STATES PATENT AND TRADEMARK OFFICE
CERTIFICATE OF CORRECTION

PATENT NO. : 5,549,887

DATED : August 27, 1996

INVENTOR(S) : Ramiro Galleguillos et al.

It is certified that error appears in the above-identified patent and that said Letters Patent is hereby corrected as shown below:

Column 19, line 9, "value of value of" should be --value of--.

Column 27, line 6 in Example 79, "Waterp$^{9)}$" should be --Water$^{9)}$--.

Column 30, line 15, "Cl$_{1-15}$" should be --C$_{11-15}$--.

Column 30, line 53, "mixture" should be --mixtures--.

Signed and Sealed this

Twenty-eighth Day of January, 1997

Attest:

BRUCE LEHMAN

*Attesting Officer*   *Commissioner of Patents and Trademarks*